United States Patent [19]
Brunk et al.

[11] Patent Number: 5,350,502
[45] Date of Patent: Sep. 27, 1994

[54] APPARATUS FOR FLUID TREATMENT OF FRAMED MEMBRANES

[75] Inventors: Donald H. Brunk, Wilmington, Del.; David J. Regester, West Grove, Pa.; Charles W. Robertson, Rockland; Anders J. Wellings, Newark, both of Del.

[73] Assignee: E. I. Du Pont de Nemours and Company, Wilmington, Del.

[21] Appl. No.: 997,820

[22] Filed: Dec. 29, 1992

[51] Int. Cl.⁵ ............... G01N 27/26; G01N 27/447; B01L 11/00; C12Q 1/68
[52] U.S. Cl. .................. 204/299 R; 204/180.1; 435/287; 435/6; 422/103
[58] Field of Search .......... 204/299 R, 180.1; 435/6, 287; 935/85, 86, 87; 436/48, 174, 175; 422/103

[56] References Cited

U.S. PATENT DOCUMENTS

| | | | |
|---|---|---|---|
| 4,725,406 | 2/1988 | Compton et al. | 422/58 |
| 4,795,562 | 1/1989 | Walsh | 210/232 |
| 4,804,469 | 2/1989 | Walsh | 210/232 |
| 4,834,946 | 5/1989 | Levin | 422/101 |
| 4,859,419 | 8/1989 | Marks et al. | 422/56 |
| 4,892,662 | 1/1990 | Walsh | 210/649 |
| 4,913,791 | 4/1990 | Hurd et al. | 204/299 |
| 4,963,236 | 10/1990 | Rodkey et al. | 204/183.2 |
| 5,047,129 | 9/1991 | Nardo | 204/182.8 |

FOREIGN PATENT DOCUMENTS

| | | | |
|---|---|---|---|
| 312252 | 4/1989 | European Pat. Off. | 435/6 |
| 9107486 | 5/1991 | PCT Int'l Appl. | 435/6 |

OTHER PUBLICATIONS

Weier & Rosette, "A Modification of the Omniblot Processing System Allowing its use in Western Blotting", pp. 258–260, 1990, *BioTechniques* vol. 8, No. 3.
"Bellco® AutoBlot™ Processor".
"WesPage™ Sheet Processing Module".

*Primary Examiner*—John Niebling
*Assistant Examiner*—Jr. Starsiak

[57] ABSTRACT

A disclosure is made of automatic apparatus for processing transfer membranes to which a blot pattern of molecular fragments has been bound so that the pattern may be optically visualized. The apparatus is characterized by at least one open processing cell and two systems for pumping; one selectively controlled to direct fluid to and from functional units and one which is closely coupled to the cell and recirculates the fluid in the cell to assure adequate and thorough treatment therein by uniform fluid flow across both sides of the membrane.

12 Claims, 8 Drawing Sheets

APPARATUS FOR FLUID TREATMENT OF FRAMED MEMBRANES

FIELD OF INVENTION

The present invention relates to apparatus for microbial detection and more particularly to membrane processing apparatus used to develop a chemiluminescent blot pattern of molecular fragments previously transferred to the membrane.

BACKGROUND OF THE INVENTION

There are several techniques directed to identification of molecular fragments wherein the fragments are deposited on a membrane (after, for example, electrophoretic separation procedures). For example, several technologies rely on the detection and identification of molecular fragments represented as a blot on a framed membrane, by imparting chemiluminescence to the blot fragments and detecting the glow pattern emanating therefrom.

U.S. Pat. No. 5,047,129 is directed to a unit for the treatment of electrophoretic strips mounted on a frame. The unit comprises at least one pair of basins and a feed, forced circulation and emptying circuit. Various liquids including different treatment liquids and a rinsing liquid are discharged through tanks with the assistance of pumps.

U.S. Pat. No. 4,963,236 is directed to apparatus and methods for isoelectric focusing of ampheric substances within fluids containing carrier ampholytes. It utilizes multichannel recycling isoelectric focusing techniques and a dual reservoir system.

U.S. Pat. No. 4,913,791 is directed to a blot frame and method of handling. Blot membranes are supported for handling during the course of blotting, analysis and storage.

SUMMARY OF THE INVENTION

There is disclosed and claimed herein apparatus for the fluid treatment of a supported membrane having first and second sides and a region containing a latent blot image thereon, comprising:

(a) a processing chamber enclosing the membrane in the region containing the latent blot image, the chamber comprising an inlet port and an outlet port;

(b) means to uniformly introduce fluid into the chamber through the inlet port, in an amount sufficient to submerge the region of the membrane containing the latent blot image;

(c) means to circulate the fluid within the chamber such that the fluid flows uniformly across the first and second sides of the membrane and the region containing the latent blot image; and (d) means to uniformly extract fluid from the chamber through the outlet port,

DETAILED DESCRIPTION OF THE INVENTION

Figure 4:
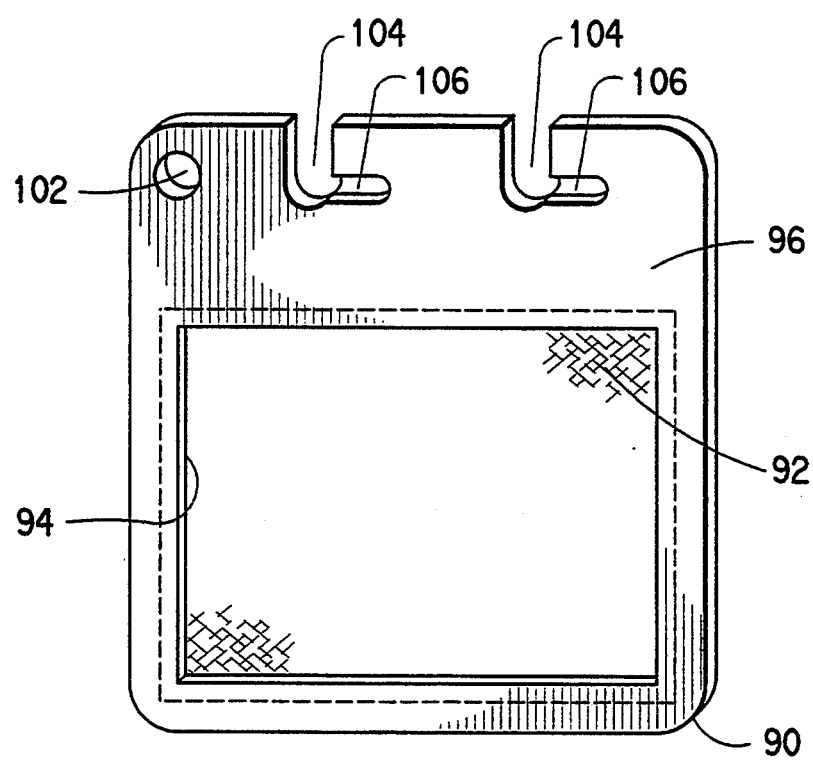
FIG. 4 is an elevational perspective view of a framed membrane.

Having reference to FIG. 4, there is shown the supported membrane used in the invention. Frame 90 holds membrane 92 bonded to two opposed edges of window 94. Note that membrane 92 is slightly larger than window 94 on both the attached and the free opposed sides. We have found that a width greater than that of the window on the two unattached sides has advantage in preventing fluid from one face transferring to the other and so interfering with uniform flow which results in a less than satisfactory image. An extended portion 96 provides a convenient grasping region for insertion by hand or by machine as will be seen. Hole 102 is for alignment in processing apparatus. Insofar as understanding this invention it must be understood that the membrane 92 has been used in a Southern Blot type transfer (we prefer direct blot) or the like and carries a latent image of the separated fragments that are generated by gel electrophoresis. The invention is also applicable to other blot processing techniques such as Western and Northern blots.

Figure 1:
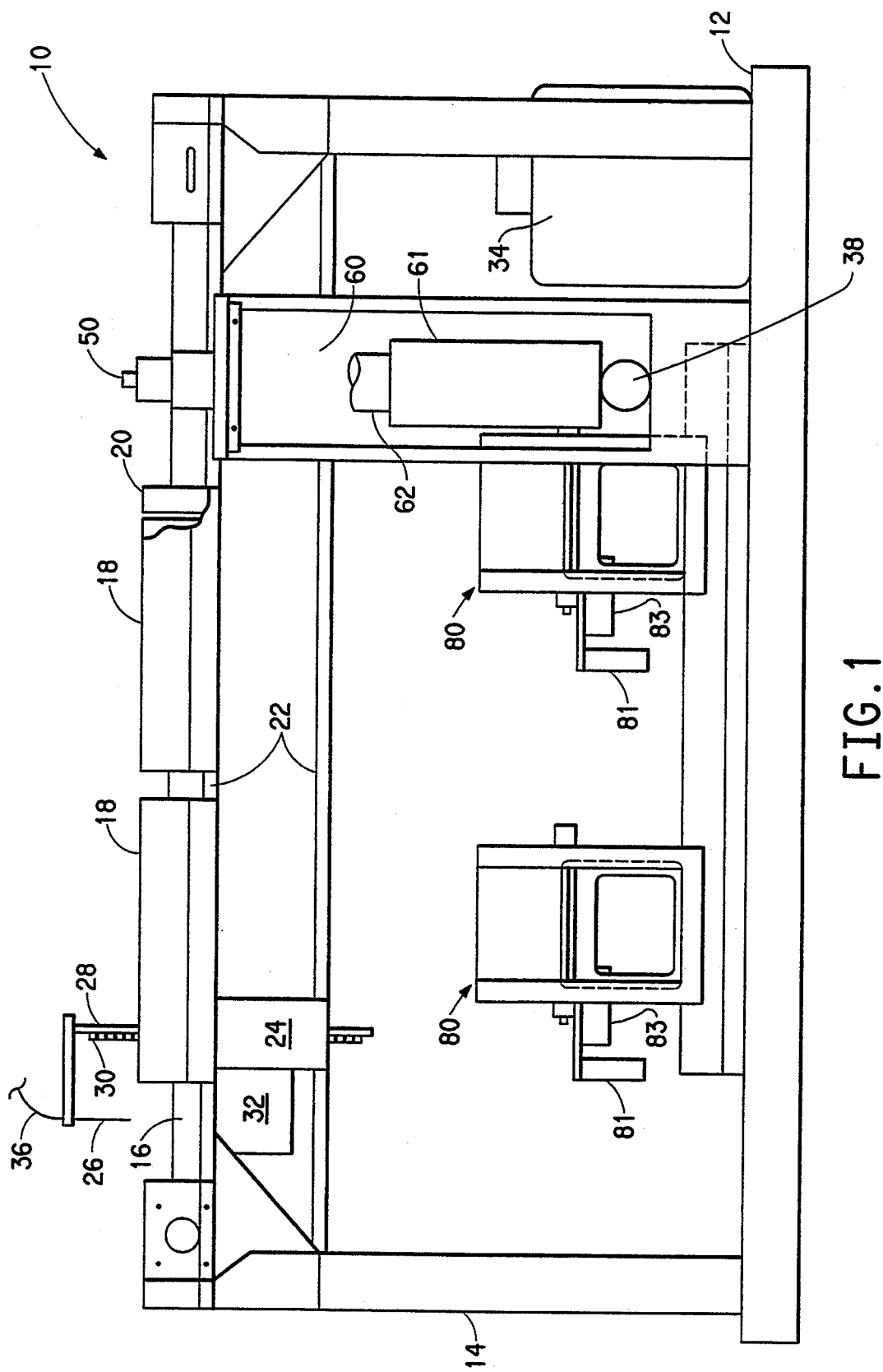
FIG. 1 is a front elevational view including a partial cross-section of a portion thereof of apparatus according to the invention.

Membrane processing apparatus 10 (see FIG. 1) comprises base 12 to which is attached structural frame 14 which is a three dimensional structure forming an inverted-U shape and suitably braced and stiffened to support a number of elements. Rack 16 holds one or more (as shown, two) reagent containers 18. Each of these has a number of in-line cells 20 which contain the needed reagents for one or more selected processes. For the application of the preferred embodiment, as will be seen in greater detail later, we provide nine cells per container (although the experimenter may select a number of cells consistent with the process of interest). Further, in our preferred procedure, each cell 20 holds 28 ml which applies enough fresh reagent to process one membrane. Again, the amount of reagent is to be selected by the experimenter. Of the nine cells 20 in a given reagent container 18 for the preferred process six hold ready-to-use reagents and three are for other possible embodiments. These six cells 20, in another embodiment, can hold reagents that need rehydration which can be done using the deionized water supply of the apparatus as will be seen. In yet another embodiment, three hold ready-to-use reagents per se and three of these cells 20 hold reagents that require rehydration within a reasonable time of use and so three cells 20 are provided with the required hydration agents and mixing is carried out in situ in three cells provided for this purpose. We prefer to supply the reagent containers as consumable items completely loaded with liquid reagent. There are two reagent containers 18 to provide a balanced work flow for an operator inasmuch as membrane processing, as we practice it, takes several hours.

Traverse rods 22 are attached to frame 14 and support traveler 24 for linear motion controllably-driven horizontally by a timing belt, pulleys and stepping motor (not shown) also mounted to frame 14. Aspirating needle 26 is mounted on vertically-translating assembly 28 which is held on traveler 24 and controllably moved via rack 30 driven by a pinion (not shown) and stepping motor 32.

Also attached to the upper part of frame 14 is needle wash station 50. Details may be seen in FIG. 2. This comprises a wash cup 70 larger in diameter than transfer needle 26. Cup 70 has a closed bottom and is centered in a drain cup 72 which gathers overflow from wash cup 70 and has a drain hole 74 which is connected by tubing 76 to waste. In use, needle 26 is inserted into cup 70 and sufficient wash fluid is pumped through the needle 26 to overflow cup 70 and wash the input tubing 36 and any other components leading into needle 26, as well as the inside and outside of needle 26. A more effective procedure first places needle 26 in drain cup 72 while the inside of the needle and tubing is flushed and then places needle 26 in wash cup 70 to wash the outside with clean fluid.

In addition to the reagents discussed above, one or more large supply containers, such as the container 34 (preferably 1 liter), stand independently on base 12. Typical contents of the container are deionized water as a general wash liquid and specialized post-hybridization and post-conjugation washes. In the preferred embodiment, we provide three such containers; a general wash fluid (deionized water); a post-hybridization wash (see Table 1), and a post conjugation wash (see Table 1). Of course all fluid containing components are integrated into a processing system as will be explained.

Pump assembly 60 also stands on base 12. This unit contains a controllable reversible drive mechanism (not shown) that operates the piston 62 of syringe pump 61. Input and output of fluids is directed by associated electrical (and, preferably, rotary) valve 38.

Figure 3:
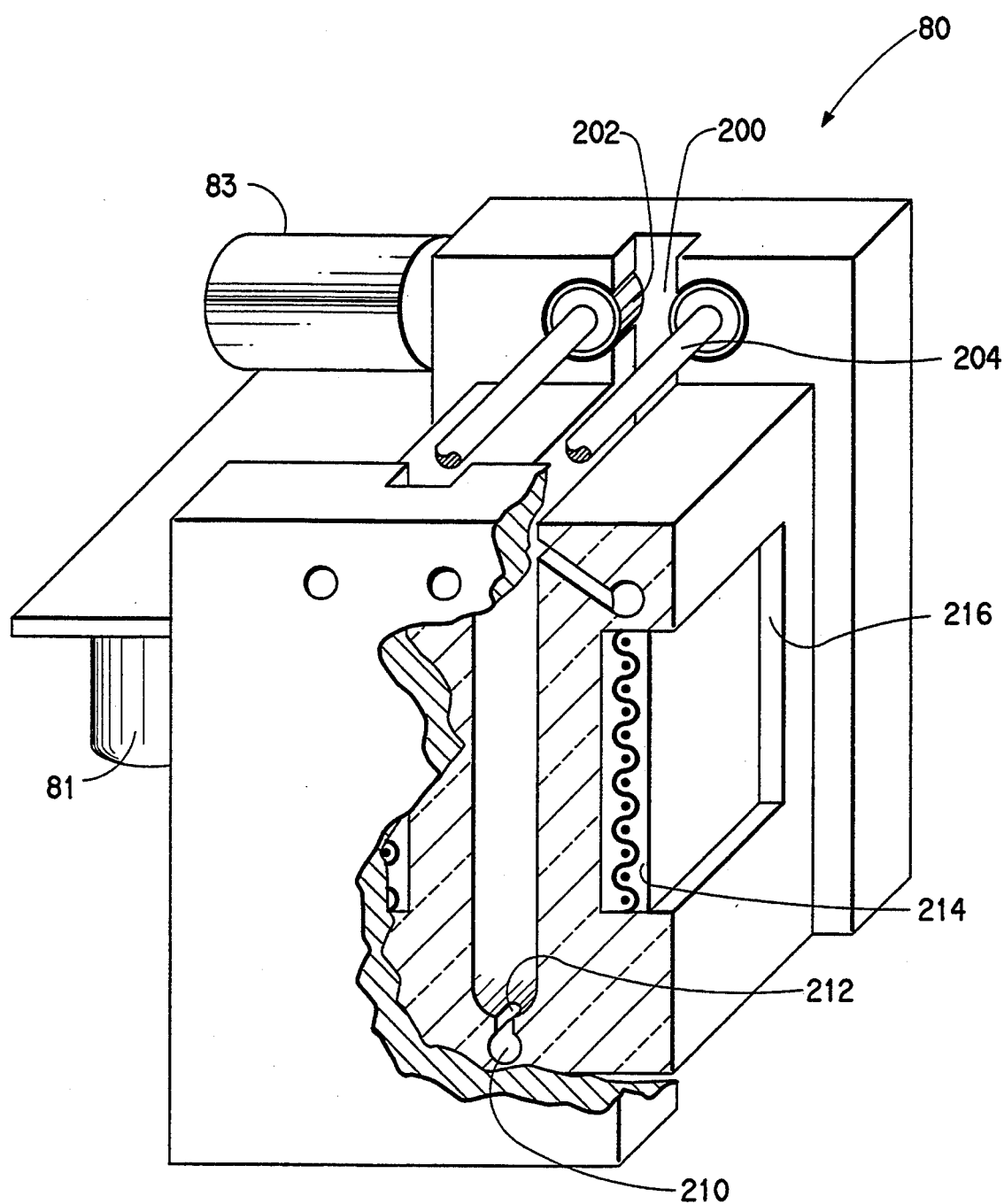
FIG. 3 is a perspective view of a membrane processing chamber of the invention with the front end partially in cross-section to show an elevational view of the interior.

Also on base 12 is one or more membrane processing chambers 80. One of these is shown in FIG. 3. The chamber sequentially processes a membrane 90 in a variety of fluids in open-topped cell 200.

The processing chamber 80 may enclose all or a portion of the membrane 90. So long as the critical area of the membrane 92 including the latent blot image is enclosed within the chamber 80, other portions of the membrane 92 may be positioned outside the chamber 80.

Figure 7:
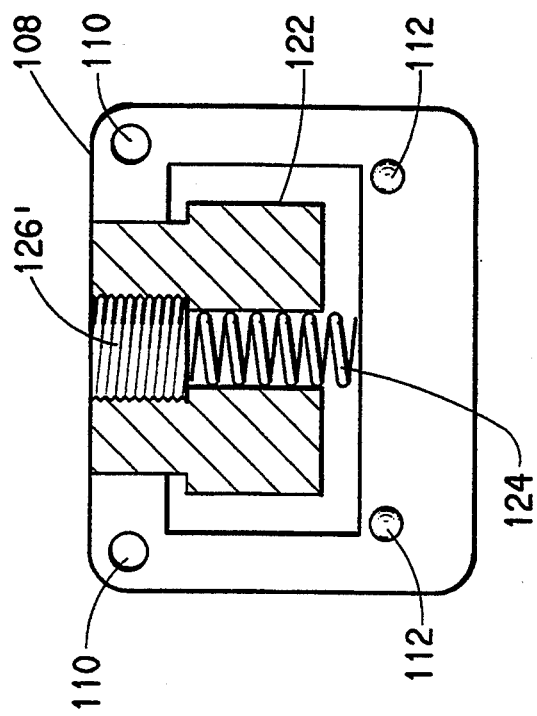
FIG. 7 is a view of the handling clip of FIG. 6 in cross section taken on the line 7—7 of FIG. 6.
Figure 6:
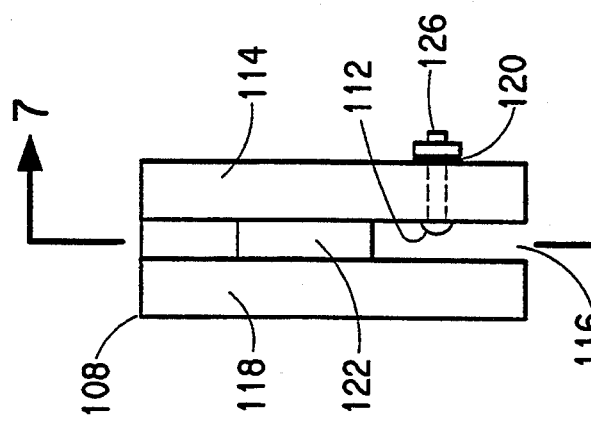
FIG. 6 is an end elevational view of a handling clip used in the more preferred embodiment.

Frame 90 is introduced into cell 200 manually or, optionally, by means to translate the supported membrane 92 into and out of the chamber 80. For example, mechanical means such as paired and opposed rubber covered rollers 202, best seen in FIG. 3, which are mounted on shafts 204 can be used and which are driven by means (not shown) such as a thumb wheel or a stepping motor depending on whether or not full or partial mechanization is provided. Rollers 202, if provided, are spaced to pinch the edges of a frame 90. Alternatively, a clip 108, as shown in FIGS. 6 and 7, may be used to translate the frame 90. The clip is suitably supported in relation to the processing chamber 80 and acts to displace the frame 90 towards or away from the chamber 80.

Figure 8:
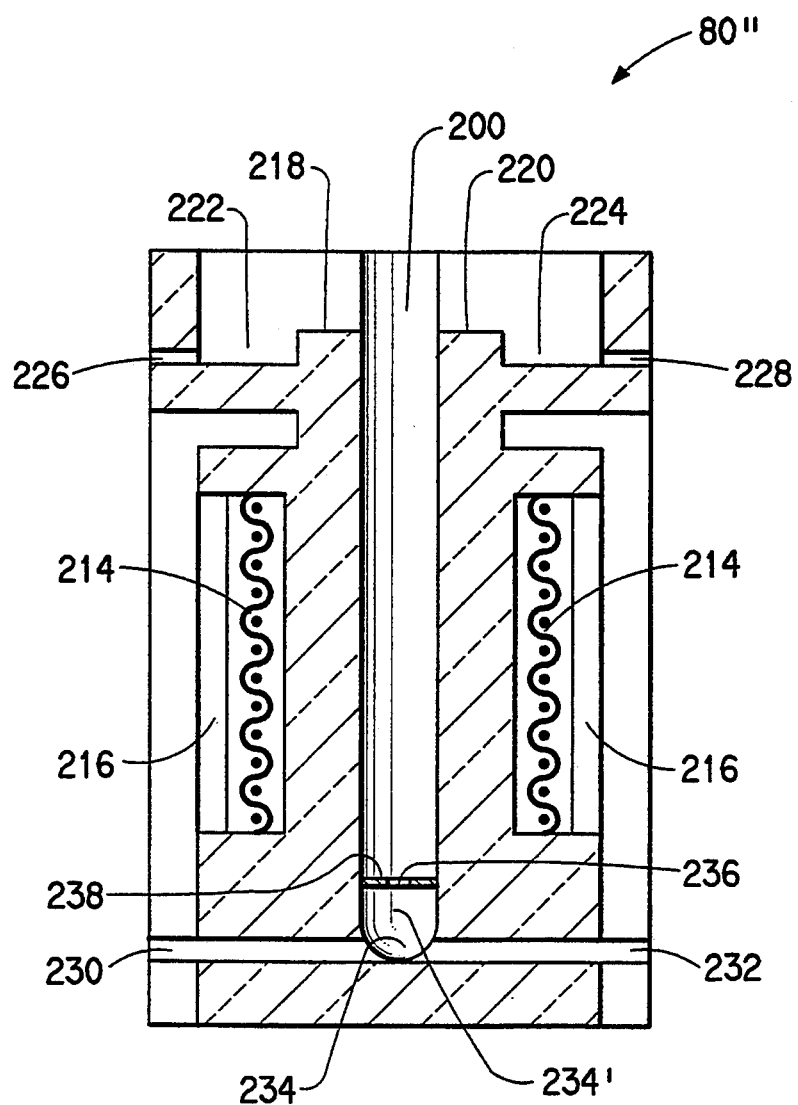
FIG. 8 is an elevational cross-sectional view of an open cell membrane processing chamber similar to FIG. 5 but modified for a still more preferred apparatus.
Figure 9:
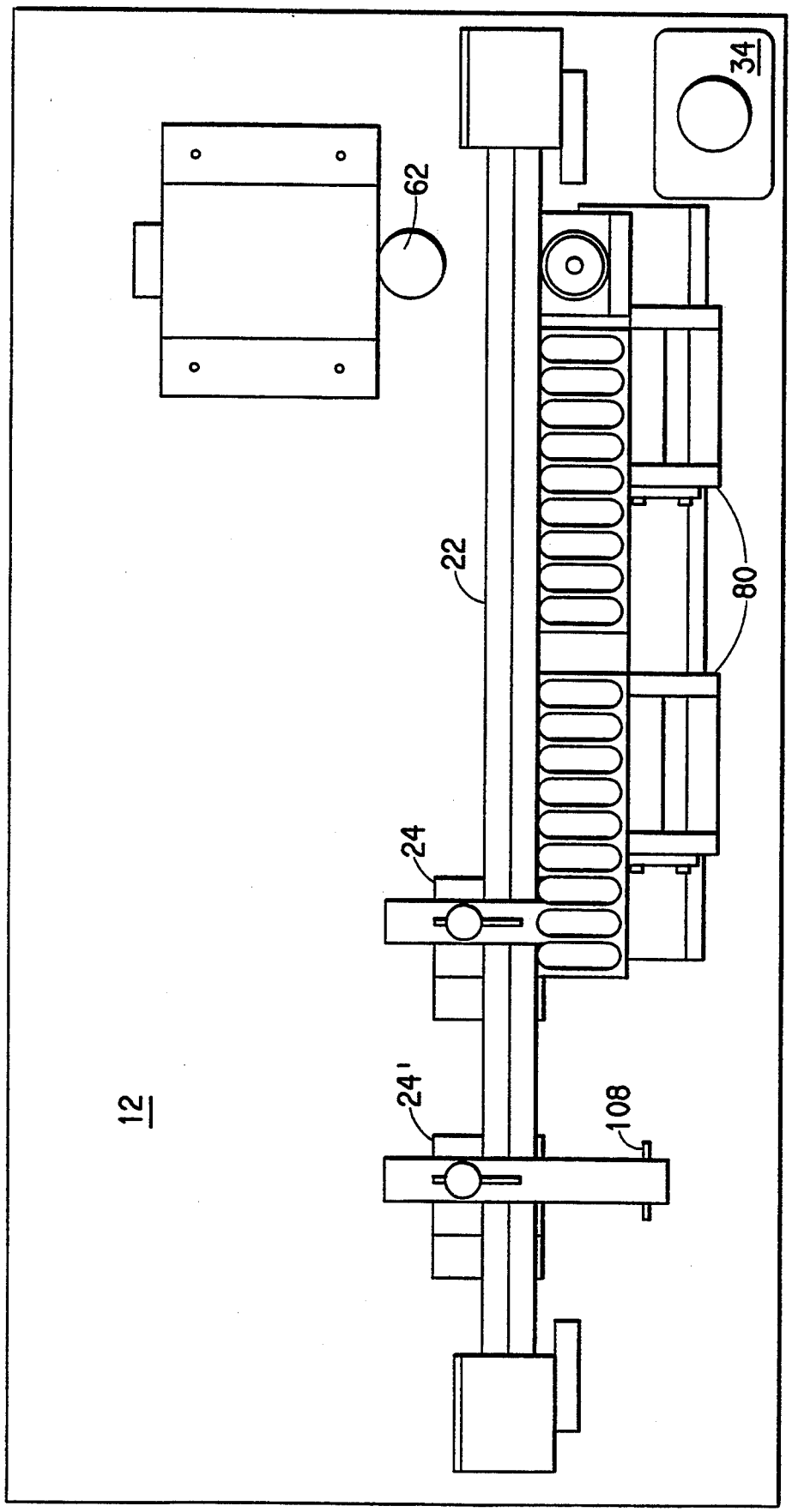
FIG. 9 is a plan view showing addition to the apparatus of FIG. 1 of a traveler assembly that positions the handling clip of FIG. 6 and uses the chambers of FIG. 8.

A further degree of automation can be provided and is more preferred. A processing chamber 80″ is shown in FIGS. 9 and 8 that is similar to that of FIG. 3 but has no components for vertical movement of the frame/membrane 90/92. Insertion and removal of frame membranes is handled by one or more clips 108 which is fastened to and moved horizontally and vertically by an additional traveler 24′ which is provided in line with at least one chamber 80′ and any other processing elements required. This traveler 24′ translates on traverse rods 22 or on an equivalent frame, and is similar to traveler 24 except that needle 26 is replaced by clip 108 which is held by fasteners not shown through mounting holes 110. See FIGS. 6 and 7. Two detent balls 112 are held by double ended leaf spring 120, itself held by fastener 126, in holes that penetrate the rear member 114 and are sized relative to slot 116 between the rear member 114 and the front member 118 so that they can not fall out. A follower 122 is biased downwardly by spring 124 held in place by screw 126′ having inwardly formed ends snapping over a receiving surface formed between members 114 and 118 to limit downward motion.

Clip 108 is used with a frame 90 and membrane 92 as shown in FIG. 4. This is topped with two slots 104 which are intersected by horizontal grooves 106. Indicator hole 102 optionally is used for automated position control.

In use, vertical motion of clip 108 toward frame 90 against a counterforce (hand or structural) inserts balls 112 into slots 104 compressing spring 124 through follower 122 as balls 112 bottom in slots 104. Horizontal motion then slides balls 112 into grooves 106 locking the two components together. The traveler 24′ can then move horizontally over a chamber 80′ and then downwardly to introduce frame 90 and membrane 92 into the chamber where release is accomplished by reverse of the horizontal/vertical motion described above aided by the ejection action of spring 124 when it is no longer resisted by a counterforce. To insure proper placement of frame 90 and membrane 92 the top of chambers 80′ may be cut away in the central region (not shown) to allow the clip 108 to enter and be closer to the bottom of the chamber upon release.

Refer now to FIG. 9. Traveler 24′ is shown installed on extended rails 22. It carries clip 108 aligned with the entries of chambers 80″. Programming of the control is adjusted so that travelers 24 and 24′ do not interfere.

Figure 2:
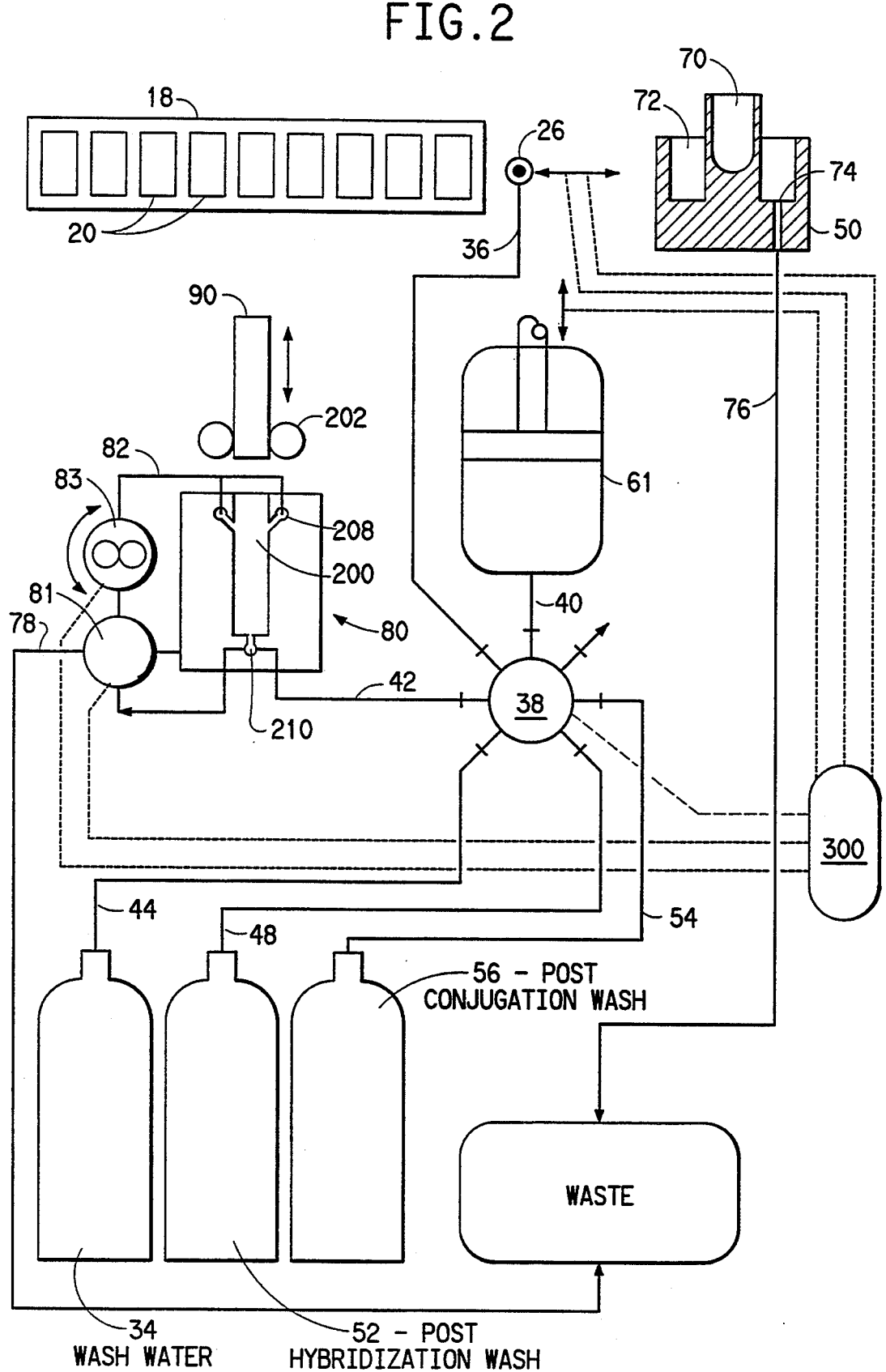
FIG. 2 is a schematic fluid flow system for the apparatus.

FIG. 8 shows the most preferred form of chamber 80″ modified from that shown in FIGS. 2 and 3 to operate with either hand insertion or, most preferably, with clip 108 and associated apparatus and to provide very uniform two-sided flow relative to the framed membrane being processed. By uniform, two-sided flow we mean a laminar flow regime in which both sides of the membrane are contacted at all points with liquid moving at equal velocity and in which the flow lines in the vicinity of both sides of the immersed blot region are parallel to the plane of the membrane. Preferably fluid enters either of two inlets 230 and 232, one closely-connected to valve 81 and circulating pump 83 in tubing 82 and the other connected to tubing 42 and thus to syringe pump 61. The entry is centered in manifold 234. Manifold 234 expands the flow two-dimensionally in plenum 234' which has contoured corners to provide smooth flow to extend to the full width of cell 200 so that fluid will flow uniformly and equally over both sides of the membrane. Optionally, distribution plate 238 with a plurality of small-diameter, evenly-spaced, distribution holes 236 further uniformizes the flow into cell 200. Upward fluid flow in cell 200 pours equally over opposing weirs 218 and 220 into sumps 222 and 224 and through outlets 226 and 228 to be connected to tubing 82 by means not shown thus draining the chamber. This configuration maintains the uniform, sheet-like flow well past the membrane and also provides a means of dispersing any bubbles or froth that may form during extended circulation.

Figure 5:
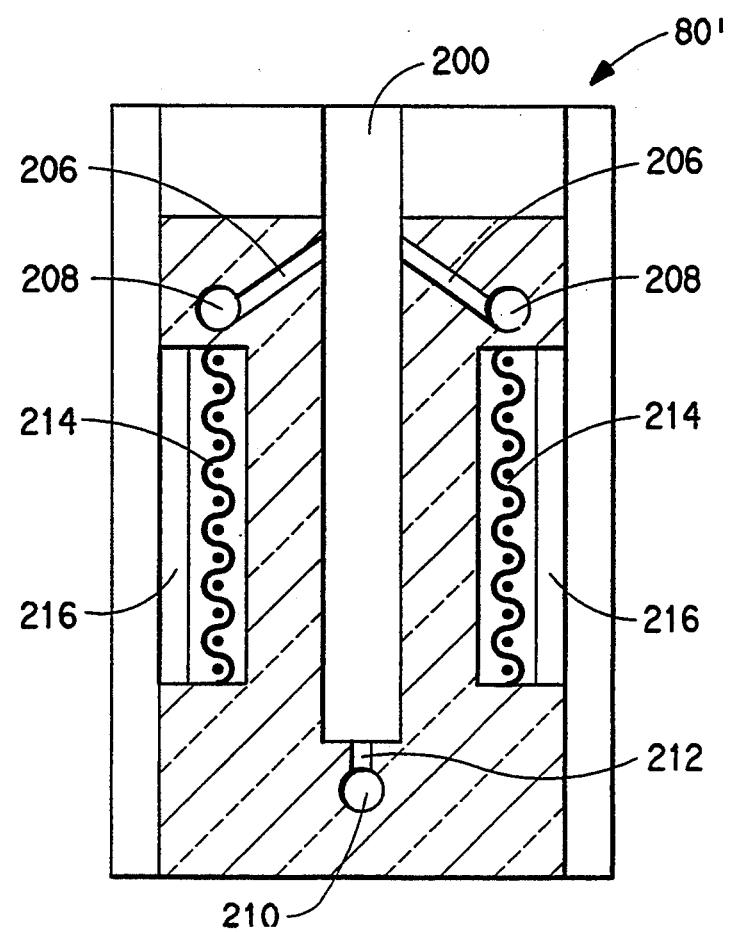
FIG. 5 is an elevational cross-section of an open cell membrane processing chamber similar to FIG. 3 but modified for another apparatus.

Chamber 80', shown in FIG. 5, is another embodiment in which the inflow proceeds through at least one manifold 210, the full width of cell 200, through a plurality of evenly-spaced, distribution holes 212 into cell 200 and uniformly upwards. Outflow is carried off by opposing arrays of evenly-spaced, distribution holes 206 into paired manifolds 208 and thence to tubing 82 by connections not shown.

Figure 12:
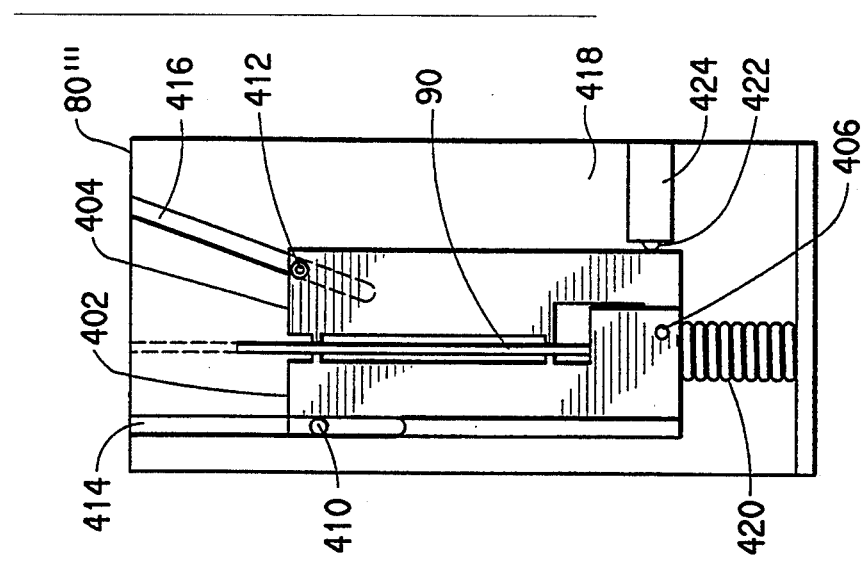
FIGS. 10, 11 and 12 are elevational cross-sectional views taken on the midline of closed cell, hinged chambers useful in still another embodiment that uses the clip of FIG. 6.
Figure 11:
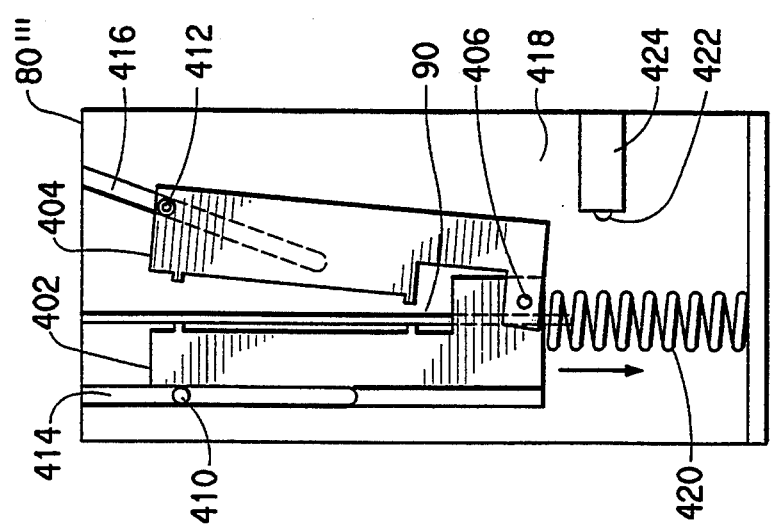
Figure 10:
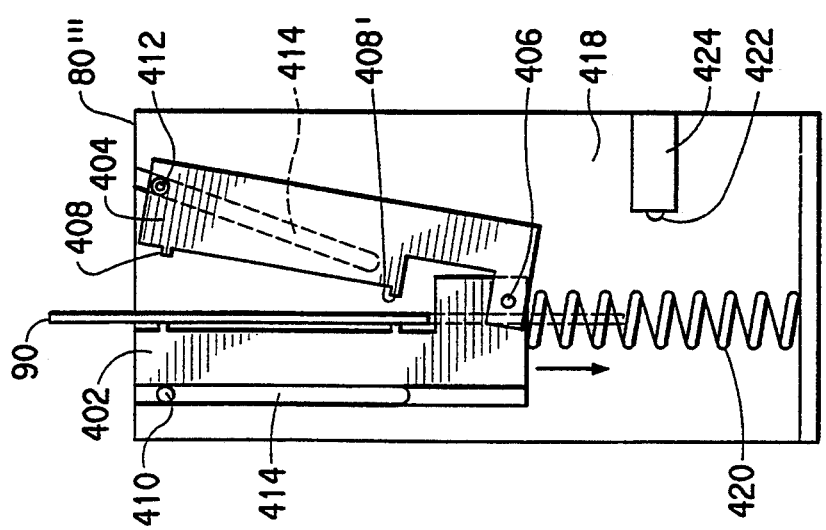

A closed cell chamber, a still further embodiment, can also be used with the clip 108 of FIG. 6. The processing chamber 80''' includes first and second enclosure portions 402 and 404 adapted to receive the supported membrane 92 between them. The enclosure portions 402 and 404 receive the frame 90 along at least one peripheral edge. Most preferably, the first and second enclosure portions 402 and 404 are joined together as by a hinge 406, so that they open to receive the membrane and then close to secure the membrane for processing operations. Such a chamber 80''' is seen in FIGS. 10, 11, and 12 showing, in that order, a progression as a frame 90 is inserted. Seals 408 and 408' close on frame 90 when the portions are closed to fully enclose and liquid-tight seal the chamber 80'''. The hinged portions 402 and 404 are each mounted on a rod 410 and 412, and each such rod is disposed in a cam slot 414 and 416 in a double sided frame 418. Cam slots 416, there being one on each side of frame 418 as indicated above, are slanted (or curved) toward hinge 406. Slots 414 are vertical. Convergence of slots 414 and 416 closes portions 402 and 404 as a frame 90 is pushed downwardly (see FIG. 11 showing partial insertion) until at full insertion the chamber 80''' is sealed shut. See FIG. 12. The pushing is generated by clip 108 locked to frame 90 as described previously. The downward motion of chamber 80''' compresses return spring 420. When chamber 80''' is fully inserted, as seen in FIG. 12, the ball 422 of ball detent 424 is thrust into a recess (not shown) on the side of chamber 80''' and hold it in position against the upward thrust of compressed spring 420. Optionally, mechanical means such as solenoid-compressed springs may be provided to add a further closing force to portions 402 and 404 when in the fully shut position. When clip 108 is moved upwardly enough forces is generated to overcome ball detent 424 as a frame 90 is held by seals 408 and 408'. As the portions 402 and 404 open, spring 420 returns chamber 80''' to the position seen in FIG. 10.

Refer to FIG. 5. Liquids are supplied and cell 200 is drained at the bottom by a plurality of distribution holes 212 which distribute the liquid across the width of the cell supplied by a manifold 210. Additionally, the means (d) to extract fluid from the chamber 80 during fluid circulation comprises paired manifolds 208 positioned so that fluid drains from the chamber 80 through a spaced plurality of distribution holes 206 so that fluid contacts the first and second sides of the membrane in uniform flow. The manifolds 208 and 210 are connected to a plurality of fluid sources. This includes at least one treating fluid, and typically at least one wash-fluid.

Metering means (e) may also be positioned in fluid connection with the manifolds 210. Metering means serve to transfer fluids from a number of fluid sources without incurring cross contamination. It also serves to circulate fluid within the chamber 80. This circulation may be assisted by the incorporation of pumping means (f) into the system. The pumping means (f) would be in fluid connection with the manifolds 206 and 210 and would circulate fluids from manifolds 206 to 210 and vice versa. In addition, the activities of the entire system may be coordinated through control means, such as a computer.

Electrical heaters 214, one on each side, are held in cavities 216. Thermocouples, not shown, control cell temperature to preset values. Circulating pump 83 (preferably a reversible gear pump) is mounted on chamber 80 so that the tubing system 82, including valve 81 (also mounted on chamber 80), is short and close coupled with cell 200.

Refer now to FIG. 2. The cells 20 of container 18 are serviced by aspirating needle 26 which moves linearly under control of control device 300 as shown by the double ended arrow. Note that control device 300 is electrically connected as shown by the dotted lines to all electrically driven or controlled devices. Needle 26 is also moved under control vertically as has been discussed above. Needle 26 is connected by flexible tubing 36 to electrically controlled valve 38 and from there by tubing 40 to syringe pump 61. Valve 38 is also connected, via tubing 42 to manifold 210 and the tubing system 82 of at least one membrane processing chamber 80 (which was described in detail above). Valve 81 also is selectively connected to waste via tubing 78. In the Figure, valve 81 could be placed above or below circulating pump 83 (and preferably at both positions) depending on draining requirements. Valve 38 is selectively connected in addition via tubing 44 to wash liquid supply bottle 34; by tubing 48 to post-hybridization wash bottle 52; and by tubing 54 to post-conjugation wash bottle 56.

The procedural steps in membrane treatment are in sequence:
Pre-clean needle and chamber; Insert membrane; Denature; Hybridize; Post Hybridization Wash; Block; Conjugate; Post Conjugation Wash; Water Rinse; Assay Buffer Treat; Substrate Treat; and Discharge membrane Table 1 lists the processing protocol including solution composition and volume and duration of treatment.

All steps except the initial cleaning require that the chamber be heated to a controlled temperature. As will be seen, a series of procedures is done at 65° C. followed by steps at 37° C. We provide heater units 214 with associated thermocouples. The heater used herein is a Minco HK5164R78.4L122B by Minco of Minneapolis, Minn. The thermocouple is a Self-Adhesive Thermocouple Assembly No. M951-K supplied by Marlin Manufacturers Co., Cleveland, Ohio. Both are adhered to a one-eighth inch thick aluminum plate. In empirical studies we have found that setting the temperature control to 72° C. provides us with the desired 65 degree chamber temperature and a setting of 39°–40° C. yields 37° C.

Alternatively, a heating system which senses the actual temperature can be used.

In use, reagent containers 18 are supplied with cells 20 loaded from left to right as seen in FIG. 2 as follows: Denature; Probe; Block; Conjugate; Assay; Substrate; Empty; Empty; and Empty.

The three empty cells are provided so that lyopholization of one or more of the reagents is an option. If this is done, a reagent, such as the probe and/or the conjugate, would be freeze dried to improve shelf life and reconstituted in situ by transfer of the appropriate fluid from one of the presently empty cells and mixing by alternate aspirating and discharging through needle 26.

A typical cycle will be described without the use of a reconstitution procedure:

Pre-clean Needle and Chamber

The heater is turned on (to yield 65° C.). Chamber 80 and syringe b are washed with deionized water. Syringe pump 61 aspirates fluid from wash water container 46 via tubing 44, 40 and valve 38. Needle 26 is moved over and down into cup 72 (see FIG. 2) and valve 38 connects it to syringe pump b via tubing 36, 40. A brief discharge clears out the tubing and the interior of needle 26. Then needle 26 is moved up, over and down onto cup 70 where a further discharge cleans the outside. Valve 38 connects needle 26 to syringe pump 61 via tubing 36 and 40. The syringe pump 61 aspirates fluid from container 46 and discharges it into chamber 80. Pump a circulates the wash around the local circuit of tubing 82 and valve 81 and then the valve is actuated to direct the fluid to tube 78 and waste. This is repeated preferably two times. NOTE: henceforth this step will be denoted as, "syringe/needle wash".

Insert Membrane

The operator loads a membrane which carries transferred molecular fragments into a cell 20 of a chamber 80.

Denature

Needle 26 moves over and down into the denature liquid. Syringe pump 61, connected via tubing 40, valve 38 and tubing 36 fills with 22 ml of fluid. Syringe pump 61, connected via tubing 40, valve 38 and tubing 42 alternately fills chamber 80, unfills it, fills it, unfills it and fills it. NOTE: this mixing is programmed for all such loadings and in further steps will be described simply as, "fills and unfills two times". Chamber 80 is then drained by pump 81 and tubing 78 to waste.

Wash

Syringe b is rinsed with deionized water by filling via tubing 40, valve 38, and tubing 44 and unfilling via tubing 40, valve 38 and tubing 36 to needle 26 (which has been moved up and over and down into wash station 50) through wash station 50 and tubing 76 to waste. NOTE: this washing is only done once and is programmed between every operation and henceforth will be denoted, "syringe/needle wash".

Hybridize

Needle 26 is raised, moved over and lowered into the hybridization cell and syringe pump 61 aspirates 22 ml of the fluid and, as before, fills and unfills chamber 80 two times. A syringe/needle wash is conducted. After 40 minutes have elapsed, valve 81, as before, drains chamber 80 to waste. A syringe/needle wash is conducted. The heater is reset to the low set point, 37°.

Post Hybridization Wash

Syringe pump b connects to container 52 via tubing 48, valve 38 and tubing 40, fills and then discharges to chamber 80 via tubing 40, valve 38 and tubing 42. Washing is assured by recirculating three 37 mL washes for 150 seconds each at a flow rate of 400 ml per minute. A syringe/needle wash is then conducted.

Block

Needle 26 and syringe pump 61 aspirate fluid out of the blocking cell 20 and fill and unfill chamber 80 two times. A syringe/needle wash is then conducted. After a five minute treatment, drain via circulating pump 83, valve 61 and tubing 78 to waste.

Conjugate Incubation

Conjugate incubation is carried out by needle 26 and syringe pump 61 which draws from the appropriate cell 20. Chamber 80 is filled and unfilled two times, followed by a syringe/needle wash. After 30 minutes elapse, valve 81 and tubing 78 drain to waste.

Post-conjugation wash

Syringe pump 61 connects to container 56 via tubing 40, valve 38 and tubing 54 and then to chamber 80 via tubing 40, valve 38 and tubing 42. Washing is assured by recirculating three 37 mL washes for 150 seconds each at a flow rate of 400 ml per minute A syringe/needle wash is then conducted.

Water Rinse

The chamber is subjected to two flow through washes using syringe pump 61 (flow up and out at a rate of about 5 mL per minute) with final draining using circulating pump 83.

Assay Buffer Treat

Needle 26 is directed to pick up assay buffer from the appropriate cell 20, tubing 36, valve 38, tubing 40 and syringe pump 61. Then chamber 80 is filled and unfilled two times using pump a, valve 38, and tubing 40, 42, and drained via circulating pump 83, valve 81 and tubing 78 to waste. This is followed by a syringe/needle wash.

Substrate incubation

Chamber 80 is filled and unfilled twice as above but with substrate drawn from the appropriate cell 200. After 5 minutes elapse for treatment, a syringe needle wash is performed. Drain via circulating pump 83, valve 81, 78 to waste.

Discharge Membrane

Processing a membrane by the above procedure requires about 2 hours. Framed membranes treated as described may then be removed and transferred to a detection module in which a CCD camera senses the chemiluminescent signals which are digitized and used in a computerized identification system. This is accomplished by any of a variety of conventional methods as is readily understood by those skilled in the art.

TABLE 1

| MEMBRANE PROCESSING PROTOCOL | | | |
|---|---|---|---|
| STEP | SOLUTION | VOL/BLOT | TIME |
| Denature | 0.20M NaOH | 25* mL | fill/drain, |

TABLE 1-continued

MEMBRANE PROCESSING PROTOCOL

| STEP | SOLUTION | VOL/BLOT | TIME |
|---|---|---|---|
| Hybri-dization | 1.50M NaCl<br>2 ug/mL probe in:<br>1% sodium dodecyl<br>sulfate (SDS)<br>0.50M Tris-HCL<br>0.25M NaCl<br>pH = 7.50 | 25 mL | 2×<br>40 min |
| Post-hyb. wash | 0.1% SDS<br>0.05M NaCl | 37 mL/wash<br>@400 mL/min | 150 sec/<br>wash, 3× |
| Blocking | 0.5 I-Block TM<br>(Tropix, Bedford, MA)<br>0.3% Tween-20[1] in<br>phopsphate buffered<br>saline (PBS) | 25 mL | 5 min |
| Conjugate | conjugate in<br>blocking<br>solution | 25 mL | 30 min |
| Post-conj. wash | 1.0M NaCl<br>0.1% Tween 20<br>0.05M Tris-Hcl<br>pH = 7.4 | 37 mL/wash<br>@400 mL/min | 150 sec/<br>wash, 3× |
| Assay Buffer | 1 mM $MgCl_2$<br>0.05M $NaHCO_3$<br>pH = 9.50 | 25 mL | fill/drain |
| Substrate | 0.25 mM PPD[2]<br>1 mM $MgCl_2$<br>0.05M $NaHCO_3$<br>pH = 9.50 | 25 mL | 5 min |

*22 mL is active amount
[1]polyoxyethylene sorbitan monolaurate, from BioRad Laboratories, Richmond, CA
[2]4-methoxy-4-(3-phosphatephenyl)spirol[1,2-dioxetane-3,2'-adamantine]disodium salt, from Lumigen, Inc., Detroit, MI The above tests were conducted using Biodyne TM transfer membranes, Part No. BNBZF3RT, a commercial product of Pall BioSupport Division, Glencove, N.Y.

What is claimed is:

1. Apparatus for the fluid treatment of a supported membrane having first and second sides and a region containing a latent blot image thereon, comprising:
   (a) a processing chamber enclosing the membrane in the region containing the latent blot image, said chamber comprising an inlet port and an outlet port;
   (b) means to uniformly introduce fluid into said chamber through said inlet port, in an amount sufficient to submerge the region of the membrane containing the latent blot image;
   (c) means to circulate the fluid within said chamber such that the fluid flows uniformly across the first and second sides of the membrane and the region containing the latent blot image; and
   (d) means to uniformly extract fluid from said chamber through said outlet port; wherein said processing chamber (a) further comprises first and second enclosure portions adapted to receive the supported membrane therebetween along at least one peripheral edge thereof, and means to translate the supported membrane into and out of said chamber (a).

2. The apparatus of claim 1 wherein said first and second enclosure portions are joined together in a hinged relation, so that said enclosure portions provide an open position which accommodates the receiving of said supported membrane and a closed position so that said supported membrane is secured therebetween.

3. The apparatus of claim 1 wherein said means to translate the supported membrane comprises at least one pair of opposed rollers suitably supported in relation to said processing chamber (a) and which contact the supported membrane therebetween along a peripheral edge thereof, which act in concert to displace the membrane toward or away from said processing chamber (a).

4. The apparatus of claim 1 wherein said means to translate the supported membrane comprises one or more clips suitably supported in relation to said processing chamber (a) and which attach to the supported membrane, which act to displace the membrane toward or away from said processing chamber (a).

5. The apparatus of claim 1 wherein said means (b) to introduce fluid into said chamber comprises a plurality of manifolds (i) positioned so that fluid contacts the first and second sides of the membrane, and said means (d) to extract fluid comprises one or more manifolds (ii) positioned so that fluid drains from said chamber.

6. The apparatus of claim 5 wherein said manifolds (i) are selectively connected to a plurality of fluid sources.

7. The apparatus of claim 6 wherein said fluid sources include at least one treating-fluid.

8. The apparatus of claim 6 wherein said fluid sources include at least one wash-fluid.

9. The apparatus of claim 6 further including metering means (e) positioned in fluid connection with said manifolds (ii), and being adapted to transfer fluids from a plurality of fluid sources without cross contamination, and to circulate fluid in said chamber.

10. The apparatus of claim 9 further including pumping means (f) positioned in fluid connection with said manifolds (i) and (ii) and being adapted to circulate fluids from said manifolds (i) or (ii) to said manifolds (ii) or (i), respectively.

11. The apparatus of claim 10 operated by control means.

12. The apparatus of claim 1 wherein said means (b) to introduce fluid into said chamber comprises at least one manifold (i) positioned so that fluid contacts the first and second sides of the membrane, and said means (d) to extract fluid comprises a pair of overflow weirs (ii) positioned so that fluid drains equally from both sides of said membrane and drains said chamber.

* * * * *